(12) United States Patent
Pandey et al.

(10) Patent No.: US 10,219,782 B2
(45) Date of Patent: Mar. 5, 2019

(54) POSITION CORRELATED ULTRASONIC IMAGING

(71) Applicant: NOBLE SENSORS, LLC, New York, NY (US)

(72) Inventors: Gaurav Pandey, Jersey City, NJ (US); Richard Koplin, New York, NY (US); Martin Weinberg, New Canaan, CT (US)

(73) Assignee: NOBLE SENSORS, LLC, New York, NY (US)

( * ) Notice: Subject to any disclaimer, the term of this patent is extended or adjusted under 35 U.S.C. 154(b) by 0 days.

(21) Appl. No.: 15/418,569

(22) Filed: Jan. 27, 2017

(65) Prior Publication Data

US 2017/0215841 A1    Aug. 3, 2017

Related U.S. Application Data

(60) Provisional application No. 62/288,515, filed on Jan. 29, 2016.

(51) Int. Cl.
*A61B 8/00* (2006.01)
*A61B 8/08* (2006.01)

(52) U.S. Cl.
CPC .......... *A61B 8/4245* (2013.01); *A61B 8/4254* (2013.01); *A61B 8/4263* (2013.01); *A61B 8/4488* (2013.01); *A61B 8/483* (2013.01); *A61B 8/565* (2013.01); *A61B 8/58* (2013.01)

(58) Field of Classification Search
None
See application file for complete search history.

(56) References Cited

U.S. PATENT DOCUMENTS

| 4,896,673 A | 1/1990 | Rose et al. |
| 2002/0087080 A1* | 7/2002 | Slayton .................... A61B 8/00 600/459 |
| 2006/0009696 A1 | 1/2006 | Hanover et al. |
| 2007/0299334 A1* | 12/2007 | Vilsmeier .............. A61B 90/36 600/414 |
| 2009/0012396 A1 | 1/2009 | Jones et al. |

(Continued)

OTHER PUBLICATIONS

An International Search Report and the Written Opinion of the International Searching Authority dated May 31, 2017 in connection with International application No. PCT/US17/15492.

*Primary Examiner* — Patricia J Park
(74) *Attorney, Agent, or Firm* — Baker McKenzie LLP

(57) ABSTRACT

An imaging apparatus includes a transducer, a detecting device and a processor. The transducer includes an emitter and receiver configured to detect a property of an object being scanned at a scanning location. The detecting device is configured to detect a position of the transducer relative to the object being scanned. The processor is configured to obtain, from the transducer, scan information representative of the property when the transducer is positioned at a first position; obtain, form the detecting device, position information representative of the position of the transducer relative to the object being scanned when the transducer is disposed in the first position; determine a coordinate location from the position information; associate the coordinate location with the scan information; and cause the coordinate location associated with the scan information to be stored in a storage.

27 Claims, 11 Drawing Sheets

(56) References Cited

U.S. PATENT DOCUMENTS

| | | | | |
|---|---|---|---|---|
| 2009/0306509 A1* | 12/2009 | Pedersen | ............. | G01S 15/8936 600/446 |
| 2013/0023767 A1* | 1/2013 | Mammone | ........... | A61B 8/0825 600/440 |
| 2013/0296707 A1* | 11/2013 | Anthony | ................. | A61B 8/13 600/459 |
| 2014/0290368 A1* | 10/2014 | Guo | ....................... | G01N 29/04 73/602 |
| 2015/0094089 A1* | 4/2015 | Moeglein | ........... | G06K 9/00671 455/456.1 |

* cited by examiner

POSITION CORRELATED ULTRASONIC IMAGING

CROSS-REFERENCE TO RELATED APPLICATION

This application claims priority to U.S. Provisional Application No. 62/288,515, filed on Jan. 29, 2016, the disclosure of which is incorporated herein by its entirety.

BACKGROUND

Ultrasonic imaging methods traditionally use a series of point scans called A scans arranged in a line to create a linear scan called a B scan. The A scan may involve generating a longitudinal or shear wave using a transducer and studying the received echoes. The B scans, which are slices of the imaged body may provide a 2D image of that slice of the imaged body. To create a 3D image, which may be called a C image, a series of B scans separated by a fixed distance are performed. Performing B and C scans requires that the subject of the scan be fixed (not moving) in location and the sensors are fixed on a linear track to provide stable geometry.

To convert an A-scan to a B-scan or a C-scan, a motor driven ultrasonic probe or a mechanical scanner actuated by motors or pneumatics are used, often also requiring an encoder to track the motion of the probe along the fixed track. These apparatuses are large, heavy and expensive. As such they are not portable and are unwieldy to use. The size and weight of the scanning apparatus also interferes with sensitive measurements. Alternately, other than mechanical scanning mechanisms, phased array or linear transducers may be used which have many ultrasonic transducers. However this increases the cost of the scanning apparatus and also makes it bulky.

Additionally, that the subject needs to be still throughout use is a significant limitation on the subject requiring special apparatus to hold the subject. If the apparatus is not able to hold a subject, imaging may be frustrated or not possible. For subjects that cannot be held still, such as infants or persons with certain diseases, they may have to be medicated before a scan can be performed.

Accordingly, there is a need for an improved imaging device that is less expensive, more portable and more tolerant to the movement of the subject.

BRIEF SUMMARY

The present disclosure generally relates to an imaging device that correlates position data for improved diagnostic imaging.

In an example, an imaging apparatus includes a transducer, a detecting device and a processor. The transducer includes an emitter and receiver configured to detect a property of an object being scanned at a scanning location. The detecting device is configured to detect a position of the transducer relative to the object being scanned. The processor is configured to obtain, from the transducer, scan information representative of the property when the transducer is positioned at a first position; obtain, form the detecting device, position information representative of the position of the transducer relative to the object being scanned when the transducer is disposed in the first position; determine a coordinate location from the position information; associate the coordinate location with the scan information; and cause the coordinate location associated with the scan information to be stored in a storage.

In another example, an imaging apparatus includes an ultrasonic transducer, at least one camera and a processor. The ultrasonic transducer includes at least one of a point probe and an array probe and is configured to scan a body. The at least one camera is configured to capture images of the transducer and the body. The processor is configured to determine a position of the ultrasonic transducer with respect to the body and correlate the position with scan data from the transducer.

In still another example, a method of imaging includes: performing an ultrasonic scan of an object using an ultrasonic transducer to provide scan data; determining a location of the transducer using an optical system; correlating the scan data and the location of the transducer; determining a two or three dimensional representation of the scan data; displaying the representation of the scan data on a display at a location associated with the determined location of the transducer; freely moving the ultrasonic transducer to a different location on the object; performing an ultrasonic scan of the object using the ultrasonic transducer to provide second scan data; determining a location of the moved transducer using the optical system; correlating the second scan data and the location of the moved transducer; determining a two or three dimensional representation of the second scan data; and displaying the representation of the second scan data on a display at a location associated with the determined location of the moved transducer.

BRIEF DESCRIPTION OF THE DRAWINGS

Reference is now made to the following descriptions taken in conjunction with the accompanying drawings.

DETAILED DESCRIPTION

Various embodiments of an imaging apparatus are described according to the present disclosure. It is to be understood, however, that the following explanation is merely exemplary in describing the devices and methods of the present disclosure. Accordingly, several modifications, changes, and substitutions are contemplated. For example, although the present disclosure mainly describes an ultrasonic imaging apparatus for medical imaging, the disclosed principals may be applied to other imaging devices including non-ultrasound transducers and non-medical imaging.

Figure 1:
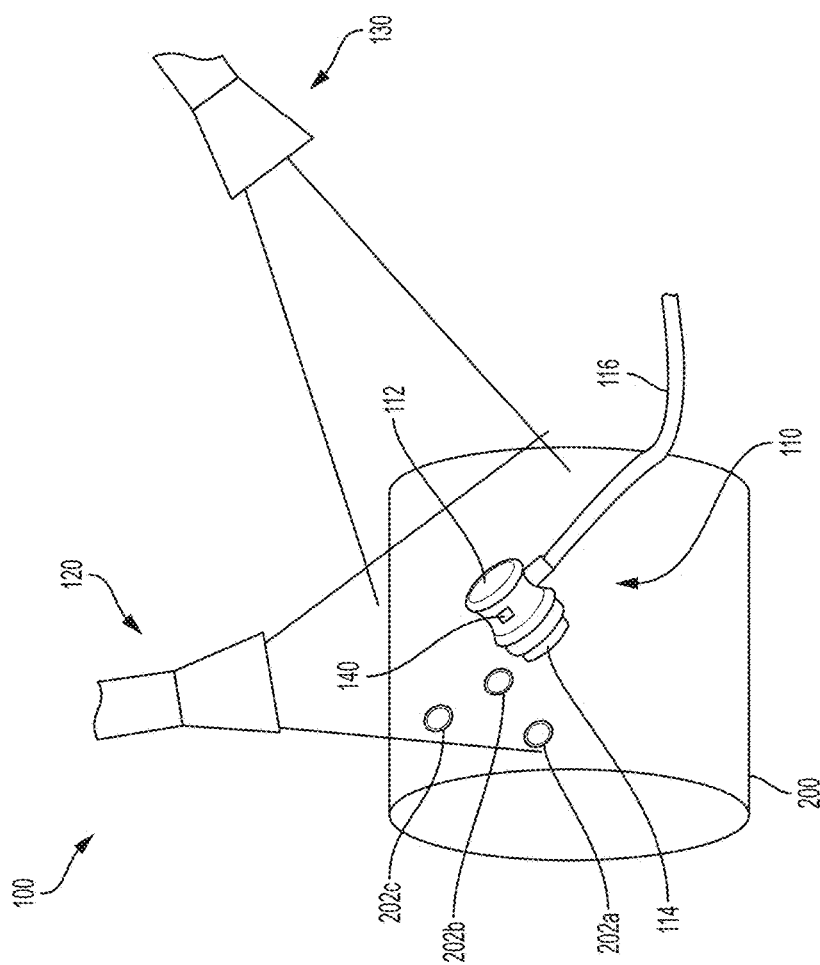
FIG. 1 is a perspective view of an exemplary imaging apparatus.

Referring to FIG. 1, an imaging apparatus 100 may include a transducer 110, which may be an ultrasonic transducer and a camera 120. The transducer 110 may include on e or more of an ultrasonic, electromagnetic, electromagnetic acoustic transducer, eddy current, x-ray or other types of single or dual point or array transducer including but not limited to a phased array ultrasound transducer. In some embodiments, a second camera 130 may also included. The camera 120 and the camera 130 may have their respective focal axis rotated with respect to a body 200 to be scanned. Different focal axis of the cameras may improve the location detection as well as provide a wider view of the body 200 to be scanned to provide a greater scan region. Two cameras are preferred for improved locating on a contoured or three-dimensional object. One camera may be preferred for two-dimensional scanning for lower overall cost. Of course, it will be appreciated that more cameras may also be included, which may provide additional accuracy and flexibility to the imaging apparatus 100.

A surface 112 on a side of the transducer opposite the transducing element 114 may include indicia such as a specific color or pattern to facilitate recognition of the transducer 120 by the camera 120 and/or the camera 130. The indicia may be visible or it may also be in the ultraviolet or infrared spectrum. Preferably, when the indicia is in the ultraviolet or infrared spectrum, the camera 120 and/or the camera 130 is capable of detecting ultraviolet or infrared emissions respectively.

The body 200 to be scanned may include one or more markers 202a-202c to facilitate recognition by the camera 120 and/or the camera 130. The indicia on the surface 112 and/or the body 200 may also be active. For example, it may include an LED and/or emit a visible, laser, infrared, ultraviolet, electromagnetic or ultrasound signal to be detected by the camera 120 and/or the camera 130. It will be appreciated that the term "camera" is not limited to an optical detector and includes any suitable detector that can identify the relative position of the transducer 110 and the body 200. The use of a non-visible emitter like an infrared LED on the transducer 110 is that image processing of the camera 120 and/or the camera 130 may be faster as the indicia is more easily distinguished from other visible entities. Particularly in the biomedical context, imaging may be performed indoors. Thus, interference with the non-visible emissions from the sun may not be significant. In some examples, multiple types of indicia may be provided in case one becomes difficult to detect, such as an infrared emitter in sunlight.

Figure 2:
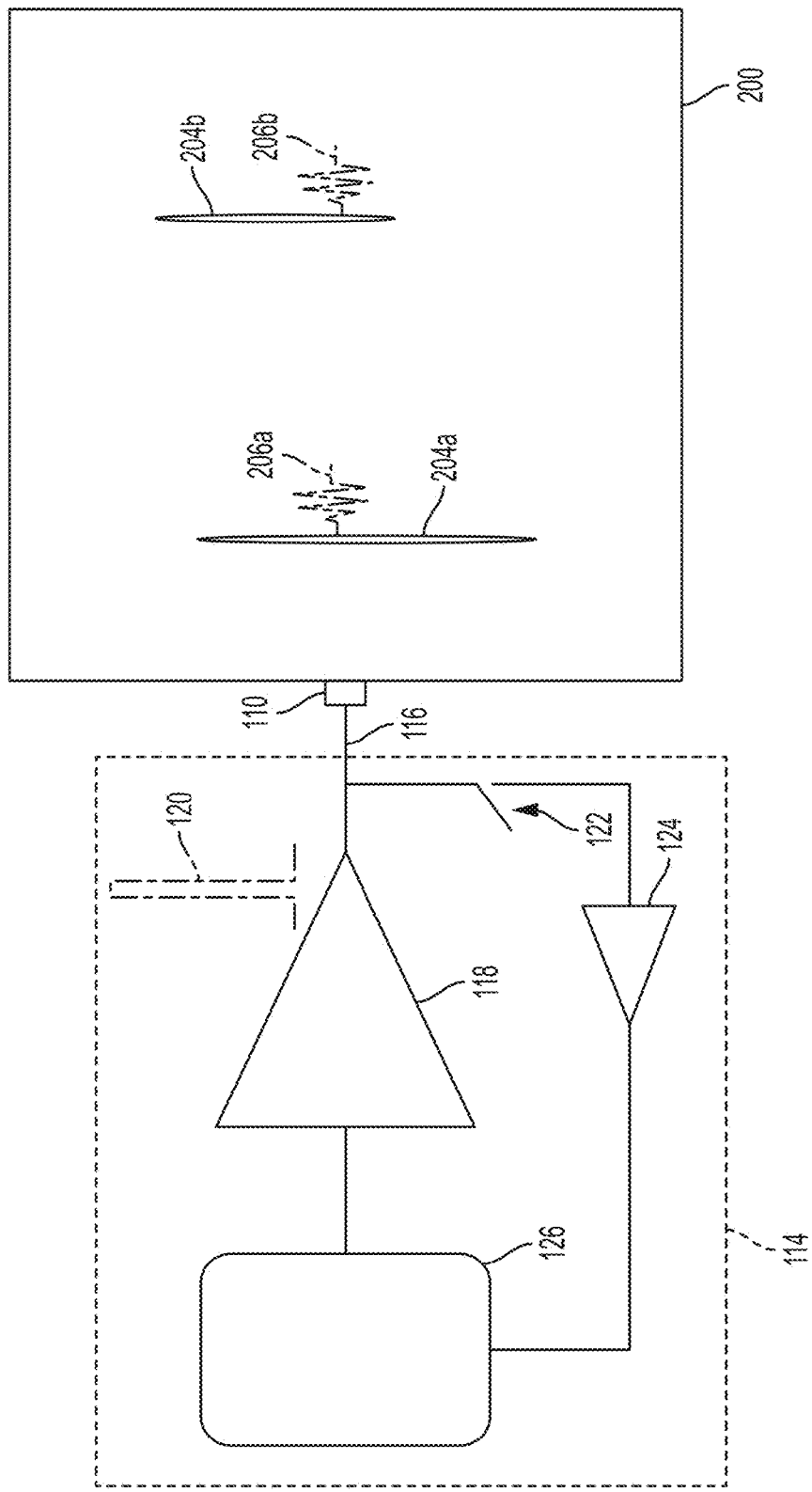
FIG. 2 is a schematic diagram of an exemplary imaging apparatus.

Referring to FIG. 2, the transducer 100 is coupled to circuitry 114. The circuitry 114 may be provided within the transducer 110 or coupled to the transducer 110 via a cable such as cable 116. A high voltage pulse generator 118 generates a high voltage pulse 120, which is emitted by the transducer 110 into the body 200. The high voltage pulse incident on the discontinuity 204a (for example a change in density or material—fluid vs flesh vs bone, etc) generates the reflected ultrasonic wave 206a. Shortly thereafter, the high voltage pulse incident on the discontinuity 204b generates the reflected ultrasonic wave 206a. After transmitting the high voltage pulse, the transmit/receive switch 122 is switched to its receive state. The transducer observes the reflected ultrasonic wave 206a and shortly thereafter the reflected ultrasonic wave 206b and supplies the received waveform through the amplifier 124 to the digital acquisition and signal processing 126. The processing 126 may determine based on the received signal (e.g., the received signal strength and received signal timing) the presence of the discontinuities 204a and 204b.

The processor 126 determines the scan data for the location of the transducer 110 at the time of the scan and stores that information. The imaging apparatus 100 may determine the location of the transducer 100 on the body 200 without requiring any special positioning apparatus via the use of the camera 120. The camera 120 may detect the location of the transducer 110, for example, by recording the position of the detected indicia on the surface 112. It will be appreciated that image recognition techniques, for example shape detection algorithms, may detect the location and orientation of the transducer without requiring any particular indicia. The inclusion of locating indicia on the surface 112 may permit less computationally complex location detection thereby leading to a lower cost device. Since the location of the camera 120 may be relatively still, the relative location of the transducer 110 may be detected which the transducer 110 is moved along the object 200. Thus, the camera 120 and/or camera 130 may be used to identify a coordinate (e.g., x, y, z) location of the transducer 110 at the time a scan is performed as well as a rotation of the transducer 110.

The calibration indicia 202a-202c disposed on the body may provide further precision in the location determination as they may be used to cancel out movement of the camera 120 and determine the coordinate position of the transducer 110 relative to the calibration indicia 202a-202c. The indicia 202a-202c may have a pattern different than and distinct from the pattern of the surface 112 to facilitate the detection of the transducer by the camera 112.

Figure 3:
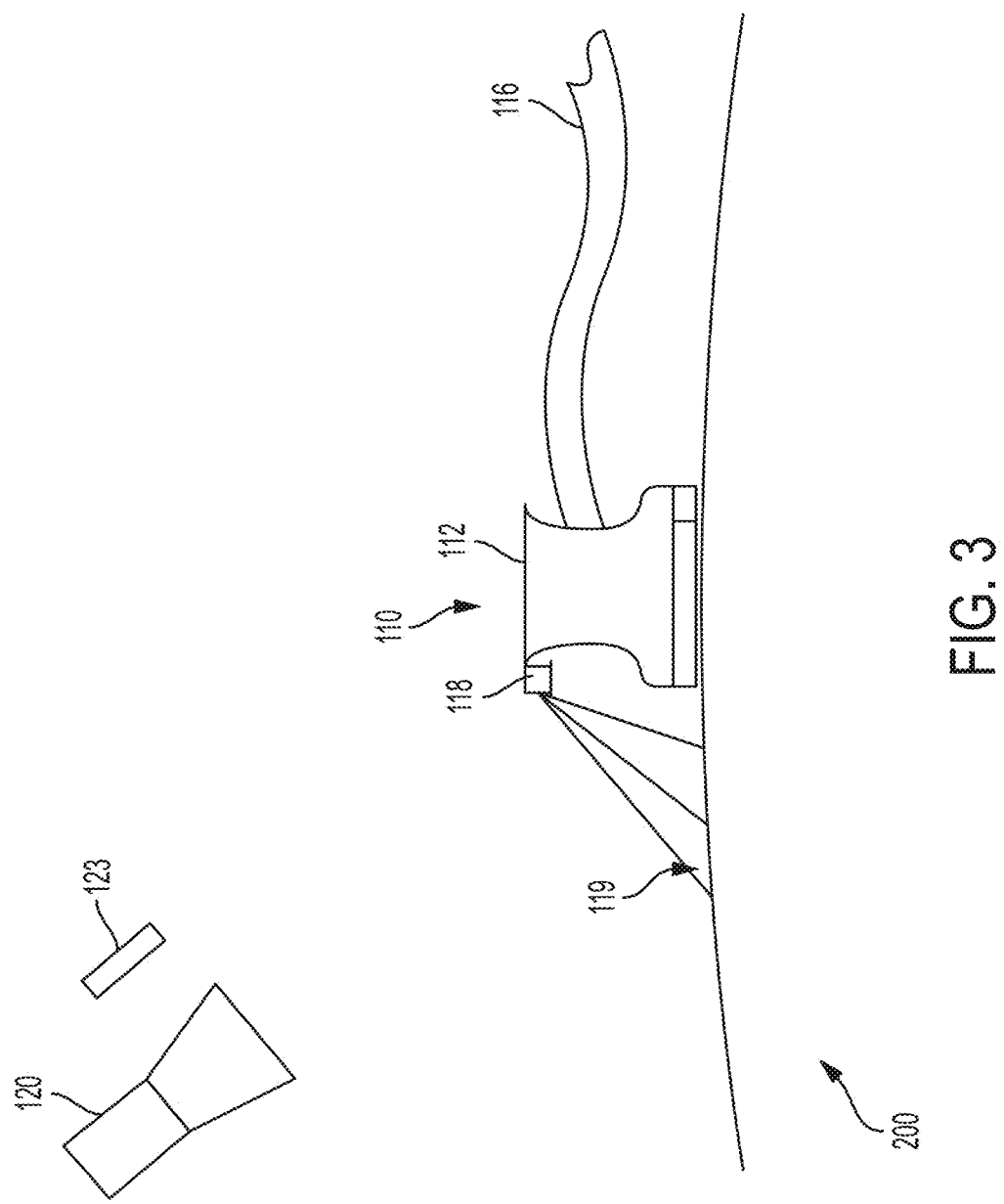
FIG. 3 is a side view of an exemplary imaging apparatus.

In some embodiments, the transducer 110 may be small and the surface 112 may be occluded from the camera's view by the hand of the operator. Referring to FIG. 3, the transducer 110 may include a projector 118 that projects a pattern detectable by the camera 120 on the body 200. The pattern 120 may be a speckle pattern of visible or not visible light. In another embodiment, a projector 123 may project a speckle pattern that is reflected or otherwise affected by the transducer 110. Distortions in the speckle pattern observed by the camera 120 may be used to determine a location of the transducer 112.

The calibration indicia 202a-202c may also be used to calibrate a position of the camera 120 (and similarly for camera 130). For example, if the indicia pattern has features of a known dimension and the camera 120 has a known focal length, then the distance between the camera 120 and the body 200 may be calculated trigonometrically. In some embodiments, the calibration indicia may be positioned or applied to the body to calibrate (e.g., set a zero point of the coordinate system), and then removed.

Another exemplary benefit of using the calibration indicia 202a-202c is that it allows for the comparison of scans of the same patient at different times by aligning the locations of the scan data in the differently timed scans. Inclusion of the photographic reference from the camera 120 and/or the camera 130 in the scan record allows for using the calibration indicia 202a-202c to align scans taken at different times.

To further facilitating aligning of scans over time, the calibration indicia 202a-202c may be provided by an implanted physical marker or other semi-permanent marker. For example, a non-visible ink or dye such as a UV responsive dye may be implanted at the scan site to provide a marker that is otherwise not perceptible during daily life. A small biocompatible marker may be inserted in the skin and the ultrasound signature from that marker may serve as a reference point to compare multiple ultrasound scans. In some embodiments, multiple implanted markers may be used to provide additional triangulation accuracy and to detect whether the markers have migrated between scans.

As noted above, it will also be appreciated that neither the calibration indicia 202a-202c, the indicia of the surface 112 or the light source (e.g., projector 118) are required. For example, a pattern detection of other image processing algorithm may be used to identify the body 200 and the location of the transducer 110 relative to the body 200.

Figure 4:
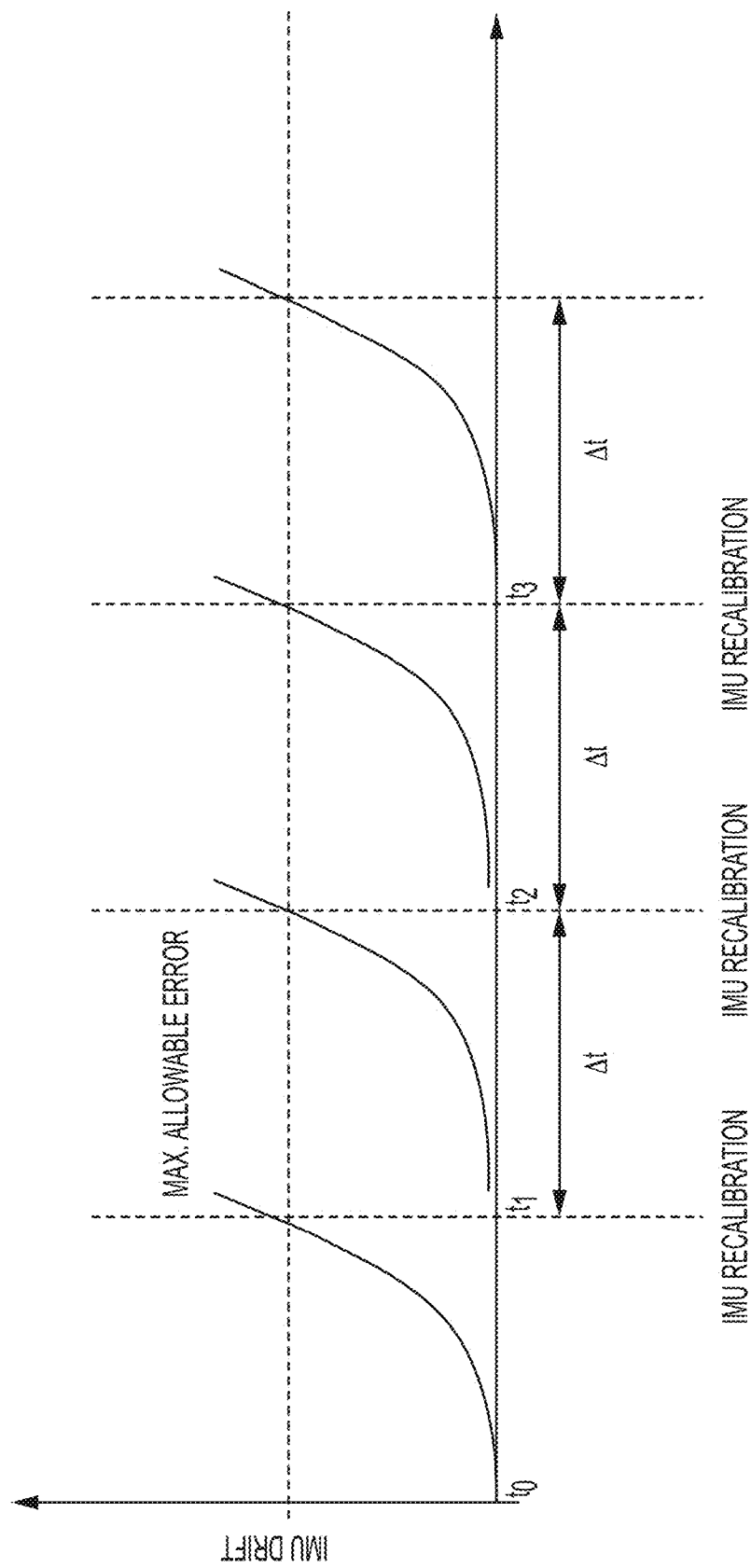
FIG. 4 is a plot of an exemplary inertial measurement calibration.

In an embodiment, the transducer 110 may include an inertial measurement unit 140 disposed inside or fixedly coupled to a housing of the transducer 110. The inertial measurement unit 140 may measure relative movements of the transducer 110 during a scan. An inertial measurement unit may include 3 axis gyroscopes and accelerometers that may track relative motion in all three (x, y and z) axis as well as rotation. The imaging device may also include a plurality of inertial measurement units, for example arranged on three axis that may be orthogonal. Preferably, an inexpensive digital inertial measurement unit is included for low cost. However, such low-cost devices are susceptible to drift, which can lead to positioning errors. With reference to FIG. 4, a position of the transducer 110 may be determined at a time t0 by detecting the position of the transducer 110 on a coordinate system using the camera 120 and/or the camera 130. This may be considered a zeroed position because it has increased accuracy of the camera based location detection. As the transducer 110 is moved, the inertial measurement unit 140 may be used to sense the relative motion and determine new coordinate locations of the transducer 110 (and therefore the location of scans performed).

As shown in FIG. 4, the drift error of the inertial measurement unit 140 increases until it reaches a point at which it is considered too significant. At time t1, the camera 120 and/or the camera 130 may be used to reset the zeroed position of the transducer 110 on the coordinate system. The same may be repeated at times t2 and t3 such that the camera 120 and/or the camera 130 is used to remove the drift error of the inertial measurement unit 140 at a specified time interval.

The recalibrations at the specified time interval may be at a pre-programmed rate or may also be predicted based on inertial measurement unit (IMU) data—for example, if the IMU movement is relatively slow, recalibration may be done at a slower rate. In another example where processing power of the imaging device may be limited, while the scan is going on, a slower recalibration rate may used to display an approximate image to the user. Camera images may be acquired in real time or near real time and stored locally or transmitted to a cloud storage along with recorded IMU data. Post-scanning, the IMU recalibration rate may be re-calculated either by the imaging device 100 itself or by a cloud server with a higher calibration rate is used to prepare a more refined the ultrasonic images.

When an inertial measurement unit is included, the position determination of the transducer 110 may be performed more quickly allowing for faster scans. The inertial measurement unit 140 may also alleviate the processing burden of location detection using the camera 120 and/or the camera 130.

Figure 5A:
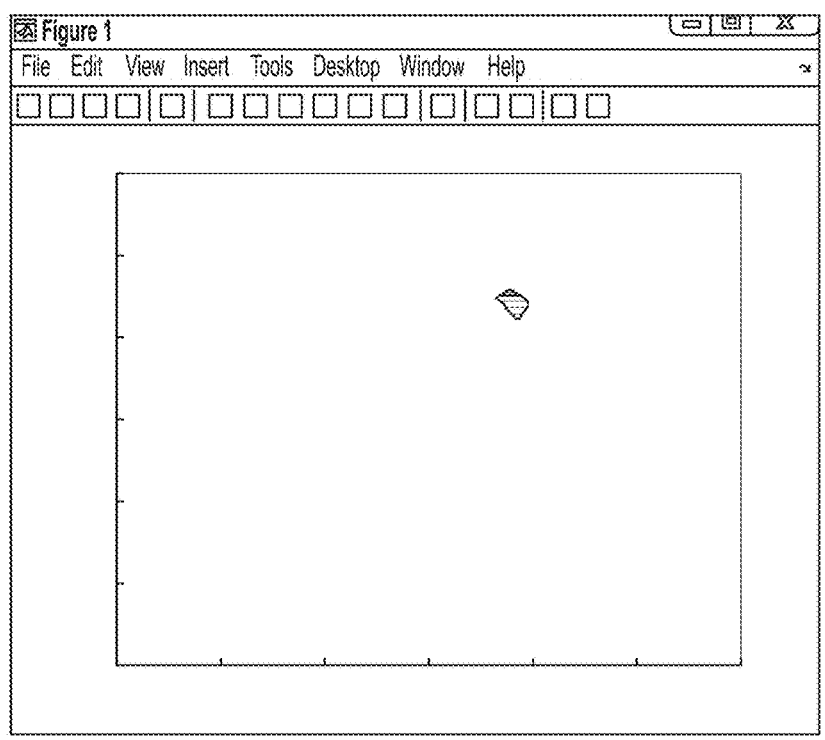
FIG. 5A is a plot of exemplary scan data.

Referring to FIG. 5A, an exemplary output plot of scan data at the beginning of a scan is shown. In this example, a location of the transducer 110 is determined by the camera 120 and/or the camera 130 to be at about 180 mm on the x axis and 225 mm on the y axis. A scan is performed (for example as discussed above with respect to FIG. 2) and the scan data is drawn at the location corresponding with the location of the transducer 110. A color of the scan data at this point may represent the type of reflection observed at that point—for example, the depth of the reflection or the type of material/tissue detected at that location.

Figure 5B:
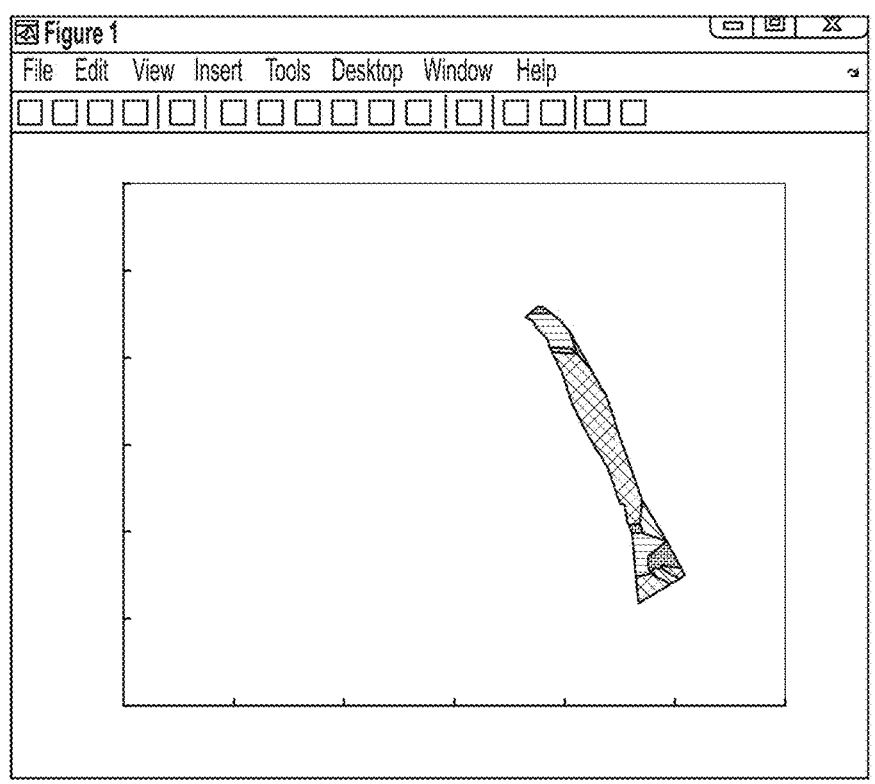
FIG. 5B is a plot of exemplary scan data.

Referring to FIG. 5B, as the transducer 110 is moved across the body 200, scans are continuously performed. For example, the transducer 110 may be moved at a rate of approximately one inch per second. The operator may be free to move the transducer in any direction and is not constrained to a fixed axis. Additionally, a flexible scan head may be provided to permit better alignment of the ultrasound probe and for more repeatable and accurate scans.

While an operator or user is discussed in the present disclosure, it will be appreciated that the flexibility of the movement of the transducer 110 according to the present disclosure, which is not required to follow a deterministic path, also improves the use of the imaging device without an operator. For example, the imaging device may be provide in conjunction with a robot to allow, for example, self-service scans at a drug store.

One particularly useful application of a robotic scan is a dermatological scan in which a robot may roughly position the transducer 110 at a similar location and the correlated position information with the scan data may be stored over time to detect small changes in anatomy.

As the transducer 110 is moved, the camera 120 and/or the camera 130 and/or the inertial measurement unit track the location of the transducer on the coordinate system. The scan data is correlated with the detected positions and the plot is updated to include the additional scan data at the locations where the scan data was obtained on the body 200.

Figure 5C:
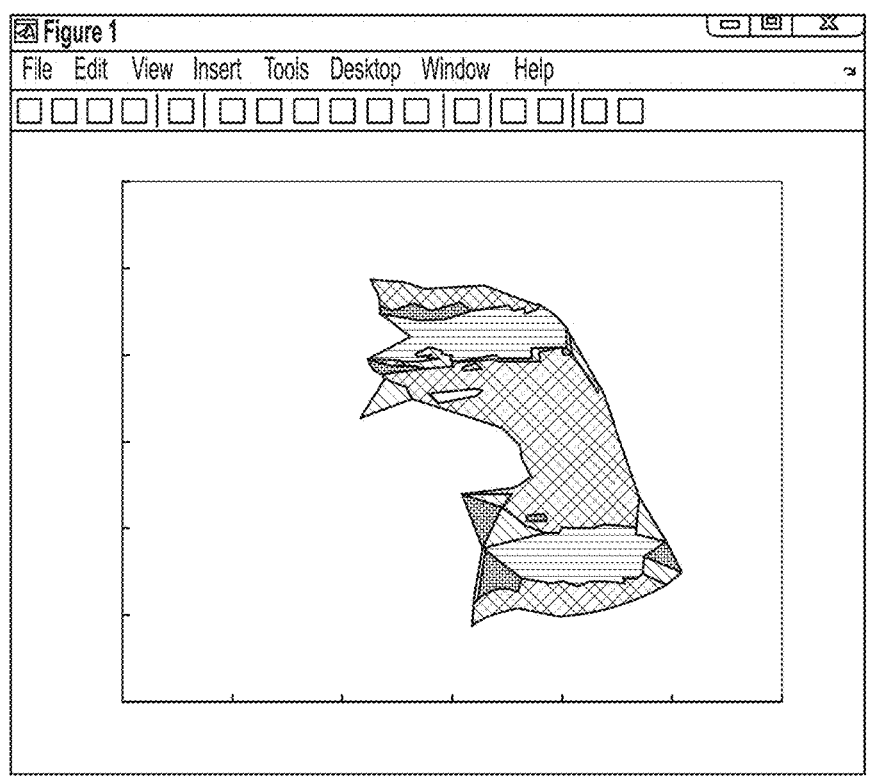
FIG. 5C is a plot of exemplary scan data.

Referring to FIG. 5C, the transducer 110 may continue to be moved along the body 200 until the entire region of interest has been scanned. The region need not be rectangular or oriented in a series of spaced slices. Any region of interest may be scanned without requiring constraints to any particular scan area or scan pattern. The collected scans that are correlated with the position information (e.g., using the coordinate system), may be stitched together using an image processor to provide two or three dimensional output. The scan data may also be colored during the scan or by post-scan processing to provide additional insight and analysis. For example, tissue types may be presented to the user based on a false coloring scheme.

In the case where the transducer 110 includes a phased array ultrasound transducer, three dimensional scans of the body 200 can be readily provide because the phased array ultrasonic transducer may provide two dimensional information at each scan point. Stitching together the 2D scans may provide the three dimensional scan of the body 200.

Figure 6:
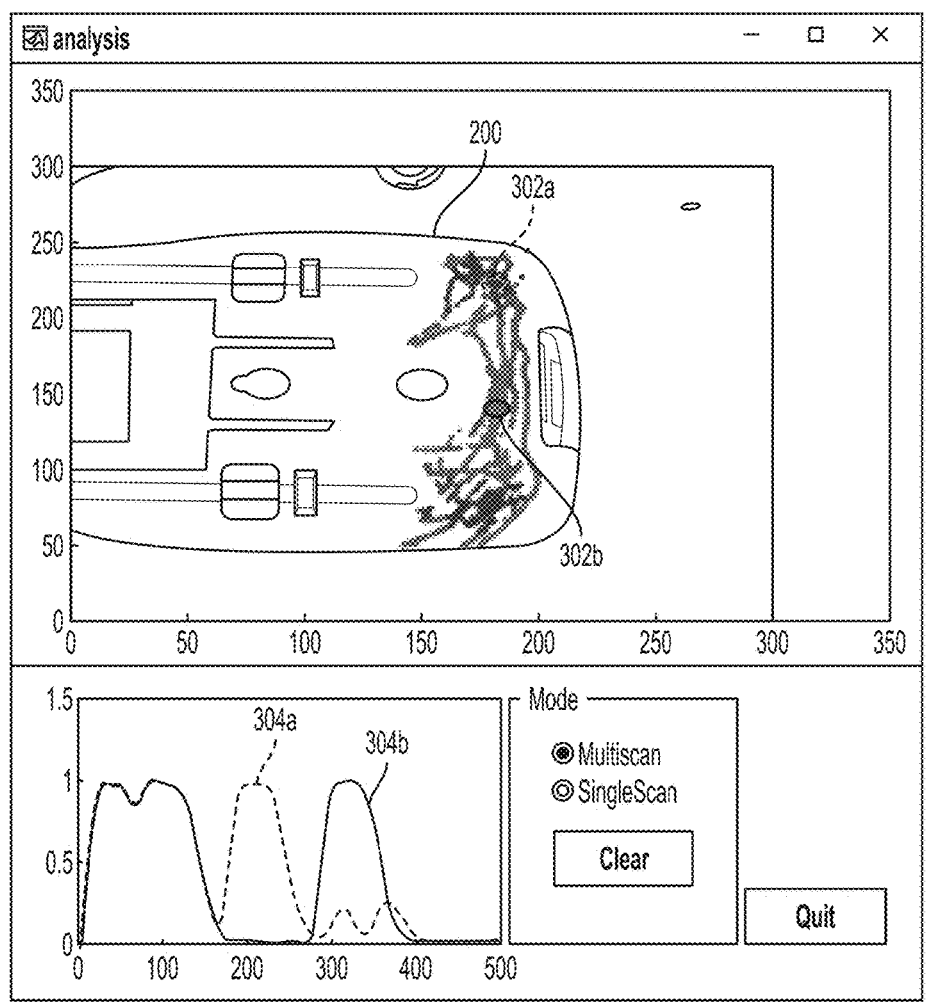
FIG. 6 is a plot of exemplary scan data.

Referring to FIG. 6, scan data may be overlaid on an image of the body 200, which can be readily obtained by the camera 120 and/or the camera 130. The scan data may be presented as a colored trace in which the color is representative of information of the scan data taken at that location such as depth of a reflection. Significant additional scan data can be provided to the user by the imaging device 100. For example, the user may select a scanned position to access the scan data, which may include raw scan data, at that location.

In the example shown in FIG. 6, the locations 302a and 302b are selected. The display includes the scan data 304a and the scan data 304b respectively associated with the locations 302a and 302b. In this example, the scan data indicates that both locations have reflection in the 0 to 150 micrometer range. At the location 302a, there is a reflection (which may indicate the presence of an object of change in density below the surface of the body 200) at about 200-250 micrometers. At the location 302b, the reflection of the additional feature is positioned at about 300-350 micrometers.

Figure 7:
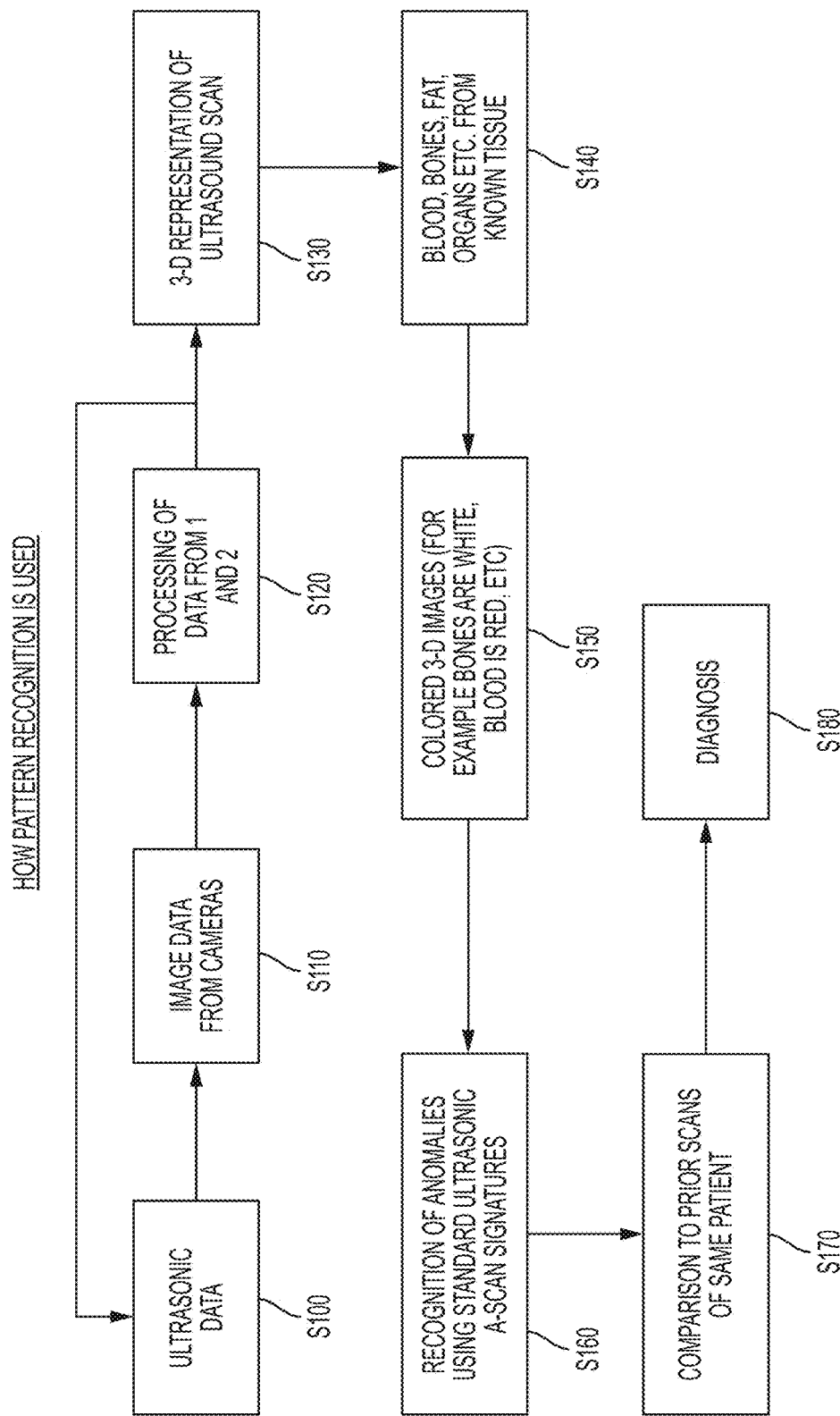
FIG. 7 is a flow chart of an exemplary scan process.

Referring to FIG. 7, a process of performing position correlated ultrasonic imaging is described. At step S100, ultrasonic scanning data is obtained from the transducer 110. At step S120, image data from the camera 120 and/or the camera 130 is obtained. It will be appreciated that the steps S100 and S110 may be performed in any order. It will also be appreciated that, particularly in subsequent iterations, the image data may be augmented or replaced with inertial measurement data in embodiments that include an inertial measurement unit. At step S120, the ultrasonic scan data from step S100 is processed with the position data from step S110 to correlate the scan data with position data and associate the scan data with a coordinate system. The steps S100, S110 and S120 may be repeated as the transducer is moved by the user until the scan is complete.

It will be appreciated that, particularly for subsequent iterations of the step S110, prior knowledge may be utilized to reduce computational demands. For example, the scan may be expected to occur at a rate such as one inch per second. Since the prior location of the transducer on the coordinate system may be known, the camera sensing field of the camera 120 and/or the camera 130 may be reduced to surround the region with the expected position of the transducer 110.

For three dimensional sensing, the optical tracking may becomes slower and slower as multiple cameras are involved. Determining the location of the transducer 110 on the coordinate system may include the calculation of disparity maps between multiple cameras. Based on the disparity maps, the three dimensional position of the tracked transducer 110 may be estimated. Disparity maps may involve significant computing resources and pattern matching and the reduction in camera sensing field may result in faster position resolution. In the example when the inertial measurement unit 140 is included, reducing the camera sensing field may also increase the calibration rate (e.g., the time interval t1-t0, etc) at which the drift error the inertial measurement unit may be reset, hence increasing resolution.

After (or during) the scanning, at step S130, the position correlated scan data may be stitched together to provide a 3-D representation of the ultrasound scan. At step S140, the correlated scan data may be analyzed to determine, for example based on depth and density measurements, properties of the scan data. Such properties may include identifying blood, bones, fat, organs, etc from know data.

Background information about the scan area and/or image recognition from the camera 120 and/or the camera 130 may be used to provide context for the identification of tissue types. For example, if an arm is being scanned, it may be expected that there will be a shallow fleshy region with bone regions at a certain depth. The user may provide a designation that an arm is being scanned or the camera 120 and/or the camera 130 may determine that an arm is being scanned using image recognition. As another example, if an abdomen is being scanned, it may be expected that there will be fatty tissue with organ regions at a certain depth. Again, the user may provide the designation that the abdomen is being scanned or the camera 120 and/or the camera 130 may determine that an abdomen is being scanned.

The detection by the camera 120 and/or 130 may facilitate more accurate results (As compared to when the region is unknown) and also a better user experience because less information and setup steps are requested of the user before the scan can be performed. An exemplary other advantage of combining camera based imaging with ultrasonic imaging is that the beamforming parameters for the transducer 110 may be selected, for example automatically optimized, based on the body part being examined.

For example, for body parts having a thicker fat layer, a higher excitation voltage may be used. The transducer 110 may be capable of transmitting multiple frequencies and in some cases, such as an array probe, multiple frequencies at the same time. Based on the determination of the body part being examined (or other input from the user), the ultrasonic scanning frequencies may be selected and those transducer elements associated with those scanning frequencies may be pulsed on. Further, based on the depth which is relevant to imaging a particular pathology, the time gain control of a low noise amplifier (e.g., the amplifier 124) may be varied.

The transducer 110 may use a front end of Analog to Digital Converter (ADC) to provide dynamic range. The gain of the amplifier may be adjusted dynamically on the fly to maintain the received signals within the range that can be processed by the ADC. This gain may be controlled automatically an in response to analog echoes received by the amplifier (e.g., the amplifier 124) and/or in response to historical information about the subject. The gain may be reduced early in the scan when there are high amplitude reflections, and the gain may be increased later in the scan when there are lower amplitude reflections. Time based controls of the gain may leverage later reflections that occur at a later time in the scan to reduce overall system noise. Depth sensing controls may be used to further tune the system for the sensing depth range and may model the gain based on time. In some cases, receivers not needed based on sensing depth may be fully switched off.

The automatic gain control curve may be adjusted on the fly for each patient depending on, for example, pathology to be scanned and prior history. For example, if a patient has a certain amount of body-fat or bone density, that may taken into account while tuning the gain curve. Data from multiple imaging techniques such as ultrasound, X-RAY, MRI over a long period of time may be combined to determine the gain curve.

For some body parts, such as the abdomen, it may be desirable to select multiple frequencies to be excited at the same time or in sequence. In the case when the transducer 110 includes a multi-modal (multi-frequency) linear multi transmit/receive device array, each array may contain multiple transmit/receive devices operating at different frequencies. Each frequency may be selected for a particular scan depth. Transmit/receive devices of the array may be switched on and off depending on scan depth needs for particular location. Turned off transmitters may reduce overall noise by ignoring certain of the receivers as well as decreasing an amount of data in the data stream from the transducer 110. Multiple arrays may be used in the transducer 110 depending on the physical coverage area desired. The use of multiple arrays in the transducer 110 may increase the speed of the scans, which may also be combined using techniques such as artificial intelligence pattern recognition because they are scanned physically together and may be combined with very close alignment for extreme accuracy.

The signal processing may also be selected based on the region of the scan. For example, different signal processing algorithms may be used for a cardiac scan and a fetal scan.

The imaging may be further improved if parameters and history of the subject and prior scans of the subject are considered. For example, the addition or loss of body fat may be first estimated using cameras. In response to detection of changes in the subject from analyzing prior images of the patient with current images obtained by the camera 120 and/or the camera 130, the ultrasonic beamforming parameters as well as signal processing algorithms may be fine-tuned based on the subjects change in body fat.

An another example of exemplary advantages during the scanning process, a desired scanning path may be determined based on a model, such as a 3D model, of the subject using the camera 120 and/or the camera 130 and/or the calibration indicia 202a-202c that may be an implanted biomarker. The are to be scanned may be determined automatically or by the user. A project, such as the projector 123 that may be a laser, optical, holographic or other type of projector, may then project onto the body 200 a region to be scanned. In some embodiments, as the scan is performed, regions that have been sufficiently scanned and have sufficient correlated scan data stored may be removed from the illuminated or identified portion of the body 200 by the projector 123. In this way, the user need only scan the body at the indicated locations until all locations have been scanned and are no longer indicated.

Of course, it will be appreciated that the order of the described steps may be changed and some or all of the optical detection and adjustment techniques described may be performed in or before steps S100, S110, S120 and S130.

At step S150, the three dimensional representation may be colored. For example false coloring technique may be used in which, e.g., bones are white, blood is read and so forth. At step S160 the A scan (e.g., point scan) information may be scanned for anomalies such as unexpected reflections. Any such anomalies may be highlighted on the display to call the attention of the user.

In some embodiments, prior scan data from the same patient may be compared with the current scan data. The position correlated scan data allows for the scan data from different scan times to be aligned and easily compared for differences.

At step S180, the scan data may be utilized for a diagnosis.

The described imaging system provides many non-limiting advantages over prior systems. For example, 2D and 3D scans can be created without the cumbersome apparatus needed for properly aligning B scans to be converted to C scans. The described imaging system provides additional freedom to the user to scan regions of an object without being constrained in motion.

An additional advantage of position correlated scan data is that not only can greater resolution be provided, but the scan data includes additional information lost in prior processing approaches and further makes it possible to correlate scans at different times to analyze for micro changes in the condition of the object. In the biomedical context, these micro changes can be significant in the early detection of disease. What might be in the normal range for all people could be a significant change for a particular person.

The imaging device may provide a biological position system for each subject based on their individual biometrics. The correlated position information associated with the scan data may be very precise. This permits a comparison of not only time history of multiple scans at the same location but also comparison of scans with a very large database of scans, taking into account considering patient info such as age, sex, ethnicity etc.

Based on the input from the camera 120 and/or the camera 130, the imaging device may identify the pathology being scanned and compare it to ultrasonic signatures (e.g., form a known database or historical) at that particular location. Based on this comparison, anomalous pathology can be detected. Of course, this benefit is not limited to the biomedical imaging area and is also applicable to other areas such as industrial imaging, for example, the inspection of aircraft part.

Comparison of ultrasonic scans at a particular position but at different times may remove of false negatives. F or example, there are a lot of false negatives in breast cancer screening based on ultrasound and x-ray (mammography). However, if successive ultrasound scans within a few weeks at the same location are compared, possible growth in suspected breast cancer can be observed. With the accurate position tracking system described herein, it may be possible to observe very fine tumor growths that are not perceptible by human eye. In addition, to further reduce false negatives, raw scan data (e.g., A scan data) may be compared with each other from many locations and pattern matching/machine learning algorithms may be utilized to further rule out false negatives.

The described imaging device may be particularly useful for dermatological imaging. In a first step, visual images of the subject from the camera 120 and/or the camera 130 may be compared with each other to identify suspected cancerous areas. In a second step, ultrasound scans may be performed at the suspected locations. Based on either single session of combined optical-ultrasonic scanning or comparison of time history of multiple such scans, skin cancer may be detected before it becomes malignant.

As another example, prior imaging techniques focus on the resultant processed image. The A and B scan data is processed to provide a C scan. The C scan is further processed to provide a human readable image. The user, for example a radiologist, attempts to find irregularities in the human readable image and may attempt to execute pattern recognition analysis on that image.

However, such analysis and pattern recognition suffers from inaccuracy and false positives because it is based upon already heavily processed data. In contrast, the described imaging system stores the actual scan data (for example the A or B scan data) along with the position/coordinate information associated with that scan data. The scan data includes much more information than a human readable image. For example, it may include an entire time/amplitude trace with all the density acoustic impedance information and reflections measured at that location. Analysis and pattern recognition may be performed on the raw scan data itself (e.g., density acoustic impedance information) to provide more accurate results and reduced false positives.

Figure 8:
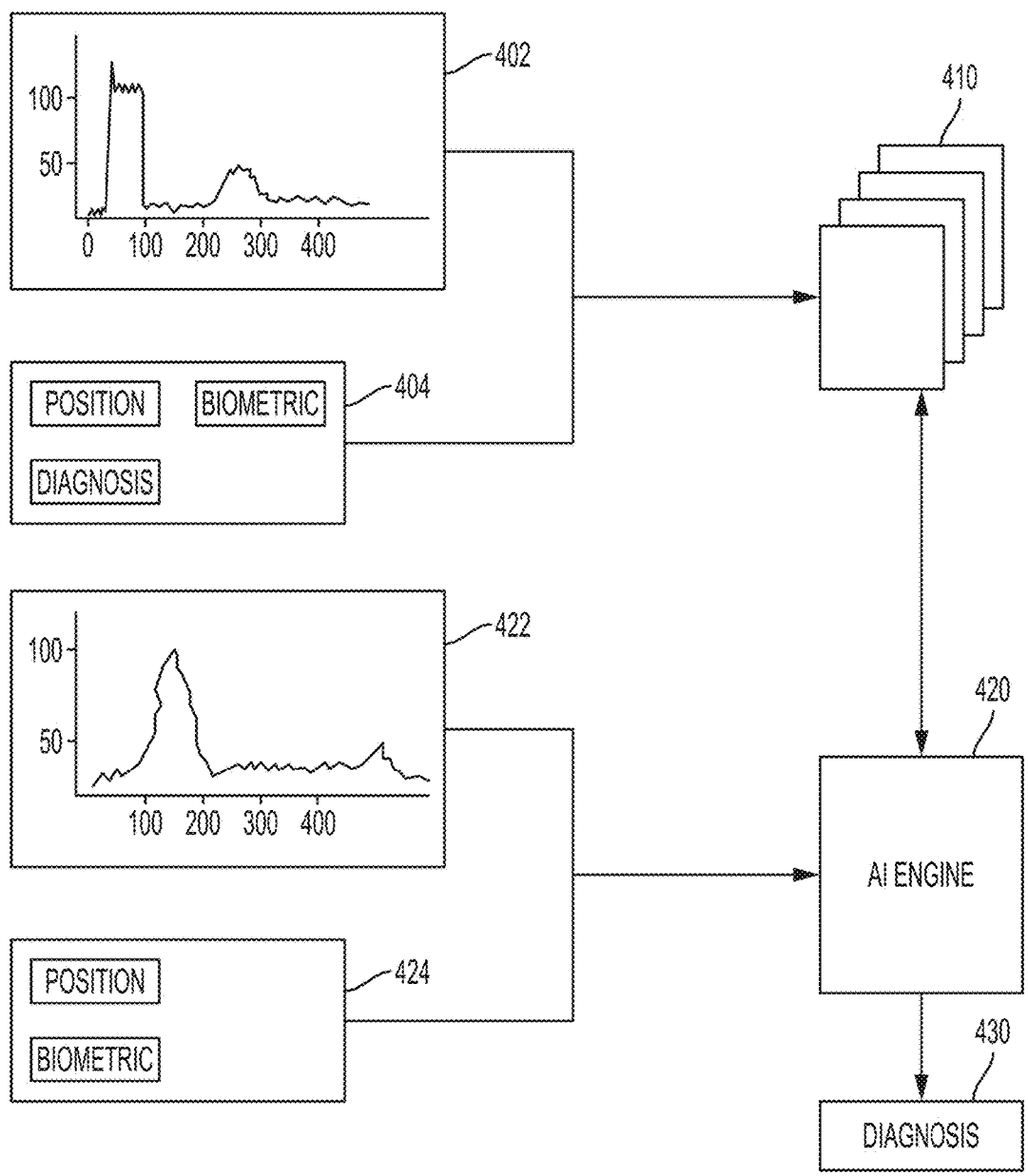
FIG. 8 is an exemplary block diagram of AI assisted diagnosis.

Referring to FIG. 8, an example of artificial intelligence (AI) assisted diagnosis will be described. Scan data 402, such as A scan data, may be associated with meta data 404 and stored in a training database 410. The meta data 404 may include information such as the position correlation for the scan data 402, biometric information about the subject of the scan data 402, and diagnosis information. When a scan is performed on another subject, an AI Engine 420 may be provided with scan data 422, such as A scan data, and meta data 424, which may include information such as position correlation for the scan data 422 and biometric information about the subject of the scan data 422. The AI engine 420 makes reference to the training database to execute searching based on the scan data itself, for example, using artificial intelligence search algorithms. The AI engine may provide, as an output, suggested diagnosis 430.

Moreover, since the transducer is not constrained in its motion and the position information may include both x, y, z, axis information as well as transducer rotation information, the time series of scan data may overlap both because the user passed over the same region more than once but also because the contour of the surface of the object causes the trajectory of the depth-wise scans to overlap. The described imaging system may take advantage of this intersecting and overlapping data to provide resultant scan data with a much finer resolution thereby further increasing accuracy.

Figure 9:
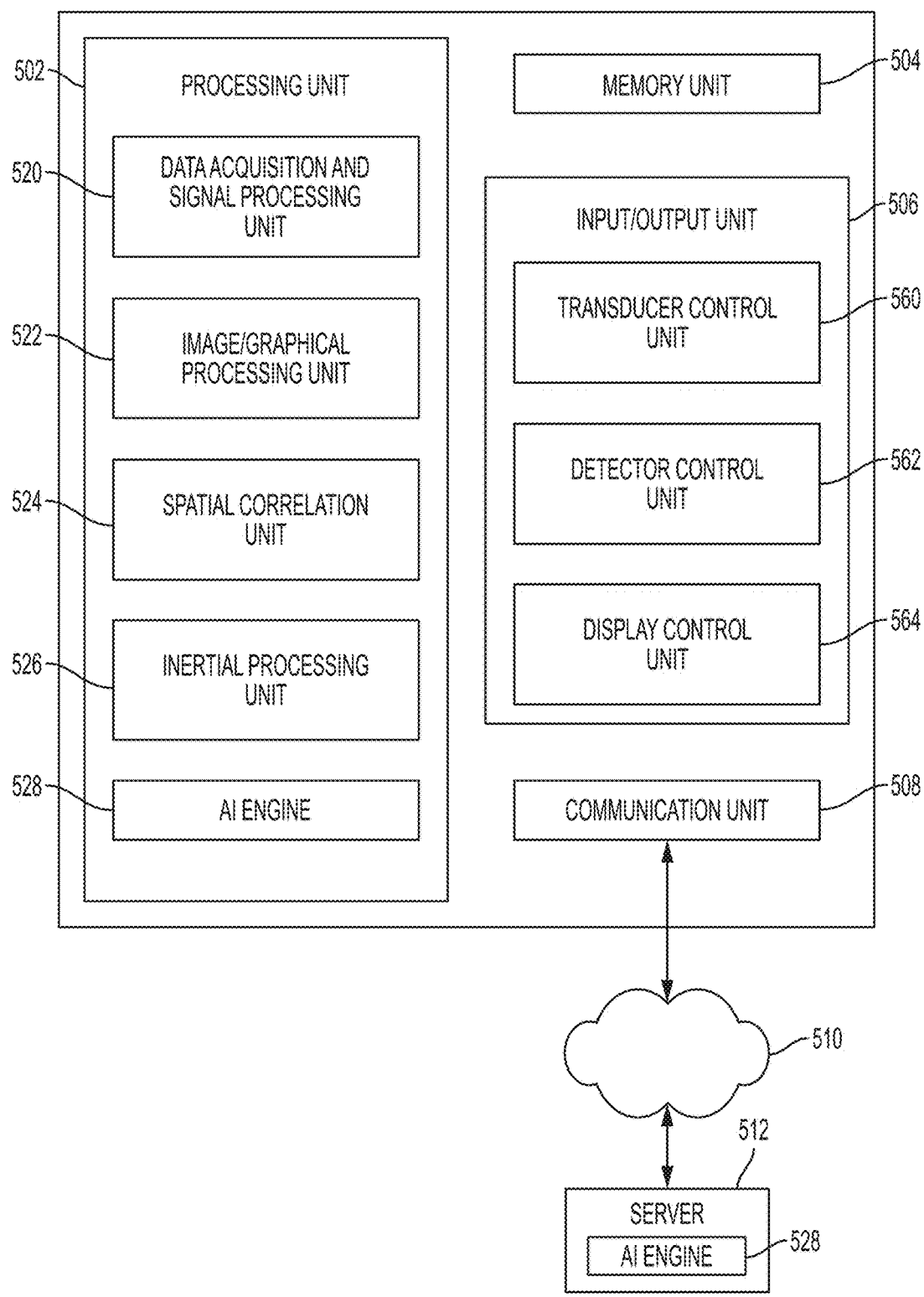
FIG. 9 is an exemplary hardware schematic diagram of an exemplary imaging device.

Referring to FIG. 9, and exemplary hardware schematic diagram for an exemplary imaging device will be described.

The imaging device may include a processing unit 502, a memory unit 504, an Input/Output unit 506, and a communication unit 508. Each of the processing unit 502, the memory unit 504, the I/O unit 506, and the communication unit 508 may include one or more subunits for performing operations associated with the imaging device described herein and may include general hardware, specifically-purposed hardware, and/or software.

The processing unit 502 may control one or more of the memory unit 504, the I/O unit 506, and the communication unit 508, as well as any included subunits, elements, components, devices, and/or functions. Additionally, while one processing unit 502 may be shown, multiple processing units may be present and/or otherwise included. Thus, while instructions may be described as being executed by the processing unit 502 (and/or various subunits of the processing unit 502), the instructions may be executed simultaneously, serially, and/or otherwise by one or multiple processing units 502 on one or more devices.

The processing unit 502 may be implemented as one or more computer processing unit (CPU) chips and/or graphical processing unit (GPU) chips and may include a hardware device capable of executing computer instructions. The use of a GPU for the image processing techniques described herein may provide advantages in processing time and accuracy particularly in the context of analyzing imaging data to detect the location of the transducer and spatially map the location of the transducer on a coordinate system.

The processing unit 502 may execute instructions, codes, computer programs, and/or scripts. The instructions, codes, computer programs, and/or scripts may be received from and/or stored in the memory unit 504, the I/O unit 506, the communication unit 508.

In some embodiments, the processing unit 502 may include, among other elements, subunits such as a data acquisition and signal processing unit 520, an image/graphical processing unit 522, a spatial correlation unit 524, and an inertial processing unit 526. Each of the aforementioned subunits of the processing unit 502 may be communicatively and/or otherwise operably coupled with each other.

The data acquisition and signal processing unit 520 may facilitate the analysis of signals received by the transducer 110 and the processing of scan data. The image/graphical processing unit may facilitate the analysis of image data from the camera 120 and/or the camera 130. The spatial correlation unit 524 may facilitate the correlation of the scan data with the position data. The inertial processing unit 526 may facilitate the processing of data from the inertial measurement unit 140. The AI engine 526a may facilitate the processing of the AI engine 420 discussed with reference to FIG. 8.

In some embodiments, the memory unit 504 may be utilized for storing, recalling, receiving, transmitting, and/or accessing various files and/or information during operation. For example, the memory unit 504 may be utilized for storing recalling, and/or updating scan data, position data, and prior scan data, for example with prior position correlated scan data far the same subject or other similar subjects. The memory unit 504 may include various types of data storage media such as solid state storage media, hard disk storage media, virtual storage media, and/or the like. The memory unit 504 may include dedicated hardware elements such as hard drives and/or servers, as well as software elements such as cloud-based storage drives.

The memory unit 504 and/or any of its subunits described herein may include random access memory (RAM), read only memory (ROM), and/or various forms of secondary storage. RAM and/or non-volatile storage may be used to store volatile data and/or to store instructions that may be executed by the processing unit 502.

The I/O unit 506 may include hardware and/or software elements to receive, transmit, and/or present information useful for performing imaging operations as described herein. For example, elements of the I/O unit 506 may be used to receive user input from a user via a user device, capture images and display information to users, and/or the like. In this manner, the I/O unit 506 may interface with a human (or nonhuman) user. As described herein, the I/O unit 506 may include subunits such as a transducer control unit 560, a detector control unit 562, and a display control unit 564.

The transducer control unit may control the operation of the transducer 110. For example, it may control the high voltage pulse generator 118 and the T/R switch 122. The detector control unit 562 may control the camera 120 and/or the camera 130. The display control unit may control the user display, for example, to generate the output illustrated in FIGS. 5 and 6.

The I/O unit 506 may facilitate the receipt, transmission, processing, presentation, display, input, and/or output of information as a result of executed processes described herein. In some embodiments, the I/O unit 506 may include one or more elements of a user device, a computing system, a server, a handheld computing device, and/or a similar device. As such, the I/O unit 506 may include a variety of elements for a user to interface with and may include a keyboard, a touchscreen, a button, a sensor, a biometric scanner, a laser, a microphone, a camera and/or another element for receiving and/or collecting input from a user, performing scans and detecting the location of a scanner during scans. Additionally and/or alternatively, the I/O unit 506 may include a display, a screen, a sensor, a vibration mechanism, a light emitting diode (LED), a speaker, a radio frequency identification (RFID) scanner, and/or another element for presenting and/or otherwise outputting data to a user or for observation by the camera 120 and/or camera 130.

The communication unit 508 may facilitate establishment, maintenance, monitoring, and/or termination of communications with other computing environments, third party server systems, and/or the like. The communication unit 508 may also facilitate communication between various elements (e.g., units and/or subunits). The communication unit 508 may include hardware and/or software elements. For example, the communication unit 508 may detect and/or define a communication protocol required by a particular network and/or network type. Communication protocols utilized by the communication unit 508 may include Wi-Fi protocols, Li-Fi protocols, cellular data network protocols, Bluetooth® protocols, WiMAX protocols, Ethernet protocols, powerline communication (PLC) protocols, and/or the like.

In an example, the communication unit 508 may communicate with a server 512 through a network 510. This may be advantageous for smaller less expensive imaging devices as the computationally complex function may be offloaded to a service, such as a cloud based service. For example, the AI driven image recognition to compare position correlated scan data (e.g., the raw scan data) discussed in the context of FIG. 8 may be performed by the AI engine 528 of the server 512. The result of the determination may be returned to the imaging device via the network 510 and the communication unit 508. AI driven image recognition can be computationally complex, which could yield high costs to implement the AI pattern recognition on the imaging device itself or even a typical server. Cost effect analysis using large quantities of scan data may still be realized with a software as a service or cloud computing model. A service provider may charge a nominal fee to perform the calculations on a high powered computing system that can perform the analysis in small fraction of the time it can be performed by the imaging device. The result can then be quickly returned to the imaging device for display to the user (e.g., via the display control unit 564) and recordation with the subject's records (e.g., in the memory unit 504 or other storage on the imaging device or a network).

It will be appreciated that the above described products, systems and methods may provide significant advantages. For example, a cost of hardware may be dramatically reduced as well as a reduction of cost and an improvement in quality and availability of diagnosis. This may provide a significant improvement in outcomes for large populations, especially in circumstances where quality care was not previously available.

While various embodiments in accordance with the disclosed principles have been described above, it should be understood that they have been presented by way of example only, and are not limiting. For example, the present disclosure is not limited to ultrasonic imaging or medical imaging.

Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

The invention claimed is:

1. An imaging apparatus, comprising:
   a transducer including an emitter and receiver configured to detect a property of an object being scanned at a scanning location;
   an imaging device external to the transducer and configured to capture an image of the transducer and the object being scanned;
   an inertial measurement unit coupled to the transducer; and
   a processor configured to
      obtain, from the transducer, scan information representative of the property when the transducer is positioned at a first position;
      determine, based on the image from the imaging device, a coordinate location of the transducer representative of the position of the transducer relative to the object being scanned when the transducer is disposed in the first position;
      associate the coordinate location with the scan information;
      cause the coordinate location associated with the scan information to be stored in a storage;
      periodically determine a calibration of the inertial measurement unit based at least in part on a location of the transducer in the images of the imaging device; and
      determine coordinate locations of the transducer between the periodic calibrations based on motion sensed by the inertial measurement unit.

2. The imaging apparatus of claim 1, wherein the processor is configured to
   obtain, from the transducer, a plurality of scan information representative of properties when the transducer is respectively positioned at a plurality of positions position;
   obtain, form the imaging device, a plurality of images of the transducer and the object being scanned when the transducer is respectively disposed in the plurality of positions;
   determine a plurality of coordinate locations respectively from the plurality of images;
   associate a plurality of coordinate locations respectively with the plurality of scan information; and
   cause the coordinate locations respectively associated with the scan information to be stored in a storage.

3. The imaging apparatus of claim 2, wherein the plurality of positions are not on a line.

4. The imaging apparatus of claim 2, wherein the imaging device includes a camera.

5. The imaging apparatus of claim 4 wherein the imaging device includes at least two cameras.

6. The imaging apparatus of claim 5, wherein the cameras have focal axis rotated with respect to each other and the object.

7. The imaging apparatus of claim 1, wherein
   the transducer includes indicia that is detectable by the detecting device, and
   the processor is configured to identify the indicia in the image.

8. The imaging apparatus of claim 7, wherein the indicia includes an ultraviolet or infrared marker.

9. The imaging apparatus of claim 7, further comprising a projector that projects the indicia onto the transducer or the object.

10. The imaging apparatus of claim 7, wherein the indicia is emitted, and the imaging device is configured to detect the emissions.

11. The imaging apparatus of claim 1, further comprising a calibration marker disposed on the object, wherein the processor is configured to detect the position of the transducer relative to the object being scanned based on the calibration marker detected in the image.

12. An imaging apparatus, comprising:
   an ultrasonic transducer including at least one of a point probe and an array probe and configured to scan a body;
   at least one camera external to the transducer and configured to capture images of the transducer and the body;
   an inertial measurement unit coupled to the transducer; and
   a processor configured to
      determine, based on the image from the camera, a coordinate position of the ultrasonic transducer with respect to the body and correlate the coordinate position with scan data from the transducer;
      periodically determine a calibration of the inertial measurement unit based at least in part on a location of the transducer in the images of the at least one camera; and
      determine coordinate positions of the transducer between the periodic calibrations based on motion sensed by the inertial measurement unit.

13. The imaging apparatus of claim 12, wherein the at least one camera includes at least two cameras, and the processor is configured to determine the coordinate position of the transducer in three dimensions.

14. An apparatus, comprising:
the imaging apparatus of claim 12; and
a server communicatively coupled with the imaging apparatus, wherein
the imaging apparatus is configured to provide correlated position and scan data to the server,
the server is configured to process the correlated position and scan data, the processing including executing a pattern recognition process with a database of scan data, and
the server is configured to provide a result of the pattern recognition process to the imaging apparatus.

15. The apparatus of claim 14, wherein the scan data includes time sequenced impedance measurements.

16. A method of imaging, comprising:
performing an ultrasonic scan of an object using an ultrasonic transducer to provide scan data;
capturing an image of the transducer and the object during the ultrasonic scan using an optical system external to the transducer;
determining a coordinate location of the transducer based on the image;
correlating the scan data and the coordinate location of the transducer;
periodically determining a calibration of an inertial measurement unit based at least in part on the location of the transducer in the image, the inertial measurement unit being coupled to the transducer;
determining coordinate positions of the transducer between the periodic calibrations based on motion sensed by the inertial measurement unit;
determining a two or three dimensional representation of the scan data;
displaying the representation of the scan data on a display at a location associated with the determined coordinate location of the transducer;
freely moving the ultrasonic transducer to a different location on the object;
performing an ultrasonic scan of the object using the ultrasonic transducer to provide second scan data;
determining a second coordinate location of the moved transducer using the optical system;
correlating the second scan data and the second coordinate location of the moved transducer;
determining a two or three dimensional representation of the second scan data; and
displaying the representation of the second scan data on a display at a location associated with the determined second coordinate location of the moved transducer.

17. The method of claim 16, wherein at least one of the determining the location steps includes determining the location based at least in part on data of the inertial measurement unit.

18. The method of claim 16, further comprising comparing the scan data with scan data of a different scan.

19. The method of claim 18, wherein the different scan is a scan of the object at a different point in time.

20. The method of claim 19, further comprising determining differences between the scan data and scan data of the different scan to detect changes in the object over time.

21. The method of claim 18, wherein the different scan is a scan of a different object.

22. The imaging apparatus of claim 1, wherein the imaging device is configured to detect the transducer to determine the position of the transducer relative to the object.

23. The imaging apparatus of claim 10, wherein the indicia is emitted by an LED.

24. The imaging apparatus of claim 1, wherein the transducer is separate from the imaging device such that the transducer may be moved independent of the imaging device during a scan of the object.

25. The imaging apparatus of claim 1, further comprising a display, wherein the processor is configured to cause the display to display an overlay of scan data of the transducer with associated locations of the scan data on an image of the object.

26. The imaging apparatus of claim 1, wherein the processor is configured to reduce a sensing field in the image based upon an expected location of the transducer.

27. The imaging apparatus of claim 1, wherein the processor is configured to adjust a recalibration rate of the inertial measurement unit based on data from the inertial measurement unit.

* * * * *